United States Patent [19]

Markovs et al.

[11] Patent Number: 5,557,030
[45] Date of Patent: Sep. 17, 1996

[54] PROCESS FOR REJECTING HEAVY HYDROCARBONS FROM LIGHT HYDROCARBONS GASES

[75] Inventors: John Markovs, Yorktown Heights; Carmen M. Yon, Carmel, N.Y.

[73] Assignee: UOP, Des Plaines, Ill.

[21] Appl. No.: 409,114

[22] Filed: Mar. 23, 1995

[51] Int. Cl.⁶ .................................................. C07C 07/12
[52] U.S. Cl. .......................... 585/826; 585/802; 95/141
[58] Field of Search .................................. 585/802, 826, 585/820; 95/141, 148

[56] References Cited

U.S. PATENT DOCUMENTS

| | | | |
|---|---|---|---|
| 4,238,204 | 12/1980 | Perry | 55/16 |
| 4,484,933 | 11/1984 | Cohen | 55/25 |
| 4,529,411 | 7/1985 | Goddin, Jr. et al. | 55/16 |
| 4,645,516 | 2/1987 | Doshi | 55/16 |
| 4,690,695 | 9/1987 | Doshi | 55/16 |
| 4,783,203 | 11/1988 | Doshi | 55/16 |
| 4,836,833 | 6/1989 | Nicholas et al. | 55/16 |
| 4,881,953 | 11/1989 | Prasad et al. | 55/16 |
| 5,181,942 | 1/1993 | Jain | 55/31 |
| 5,332,424 | 7/1994 | Rao et al. | 95/47 |

*Primary Examiner*—Glenn A. Caldarola
*Attorney, Agent, or Firm*—Thomas K. McBride; John G. Tolomei; Richard P. Silverman

[57] ABSTRACT

A process is provided for the removal of heavy hydrocarbons from a feed gas mixture. An adsorption process employing a high silica zeolite adsorbent having a silica to alumina ratio greater than about 20 and having a pore size greater than about 4.5 Angstroms is used to remove from the feed gas mixture heavy hydrocarbon contaminants and permit the further treatment of the feed gas for the bulk removal of carbon dioxide. The adsorption zone comprises at least 2 adsorption beds wherein one of the first adsorption beds is operating in an adsorption mode and the other is being regenerated. The effluent from the adsorption zone, depleted in heavy hydrocarbons is passed to a membrane treating zone to provide a non-permeate stream depleted in carbon dioxide. At least a portion of the non-permeate stream is heated and the heated non-permeate stream is used to regenerate the adsorption zone. The use of the present invention removes heavy hydrocarbon contaminants which are responsible for the degeneration of the performance of the membrane treating zone.

14 Claims, 2 Drawing Sheets

PROCESS FOR REJECTING HEAVY HYDROCARBONS FROM LIGHT HYDROCARBONS GASES

FIELD OF THE INVENTION

This invention relates to a process for the removal of heavy hydrocarbons from a gas stream to prevent membrane degradation and, more particularly relates to the use of an adsorption zone in combination with a membrane treating zone for the removal of carbon dioxide from light hydrocarbon gases.

BACKGROUND OF THE INVENTION

Natural gas as produced from a gas well presents a separations challenge. Often the natural gas is found together with other components such as sulfur compounds, water, and associated gases. The associated gases found in natural gas typically include carbon dioxide, nitrogen, helium, argon, and the like. Generally, these other gases are separated from the natural gas by bulk methods employing membrane systems. Permeable membrane processes and systems are known in the art and have been employed or considered for a wide variety of gas and liquid separations. In such operations, a feed stream is brought into contact with the surface of a membrane, and the more readily permeable component of the feed stream is recovered as a permeate stream, with the less readily permeable component being withdrawn from the membrane system as a non-permeate stream.

The inherent simplicity of such fluid separation operations constitutes an incentive in the art to expand the use of membrane systems in practical commercial operations. In this regard, it will be appreciated that the selectivity and permeability characteristics of such membrane systems must be compatible with the overall production requirements of a given application. It is also necessary, of course, that the membranes exhibit acceptable stability and do not suffer undue degradation of their performance properties in the course of practical commercial operations.

For example, in air separation applications which constitute a highly desirable field of use for permeable membranes, oxygen is typically the more readily permeable component of the feed air for particular membranes and is withdrawn as the permeate gas. In such embodiments, nitrogen is the less readily permeable component and is recovered as non-permeate gas. In air separation applications, it has been found that the performance characteristics of the membranes are sensitive to the presence of certain contaminants in the feed air stream. Exposure to such contaminants may result in a significant reduction in the permeability of the membrane in use. Fortunately, most contaminants commonly present in ambient air, such as light hydrocarbons, $H_2O$, and $CO_2$, have been found to result in, at most, a modest decrease in membrane permeability. The presence of even relatively low concentrations, e.g., less than 1 ppm by volume as $C_1$, of heavy hydrocarbon oil vapors, such as might enter the feed air stream from an oil lubricated air compressor, can result in rapid and extensive loss of membrane permeability.

It is well known in the art that selection of oil lubricated rotary screw feed compressors for the membrane permeability is subject to an initially rapid and significant decrease, followed by a further gradual decline over a period of months of operation. In response to such an undesirable decrease in membrane permeability, it is presently common membrane practice to size the active membrane surface area with a safety factor sufficiently large to compensate for the anticipated permeability loss from all sources. Initially, therefore, the membrane system is significantly oversized for the desired product flow, and the feed gas compressor is typically operated in a turndown mode. As permeability degradation proceeds, either the operating temperature or pressure, or both, are increased to compensate for the decrease in permeability. In some instances, it is necessary or desirable to by-pass some of the modules in the membrane system initially so as to reduce excess membrane area employed when the membranes exhibit their full permeability capability and subsequently to bring such by-passed modules on stream as degradation of the initially employed modules progresses. In such instances, it will be appreciated that, in addition to a significant capital cost penalty associated with the provision of extra membrane surface area, such a membrane system must operate over a significant portion of its operating life under off design conditions and that the control strategy for such a membrane system is more complex than for a system operating closer to its optimum design conditions.

As an alternative to such overdesign of membrane systems to compensate for degradation in use, attempts have been made to restore lost performance, but such efforts were initially unsuccessful in developing an economically feasible means for restoring the permeability of degraded membranes. Restoring any portion of the degraded membranes would require interruption of the gas treating operation, displacing large quantities of gas. Neither overdesign of the membrane system nor interruption of gas product operations for membrane restoration treatment, or a combination of these approaches is an entirely satisfactory means for overcoming permeability degradation in practical commercial air or other gas separation operations. Further improvement in the response to the problem of membrane degradation is highly desirable in the membrane art.

U.S. Pat. No. 4,881,953 to Prasad et al. discloses another approach to the problem of preventing premature loss of membrane capacity by passing the feed gas mixture through a bed of adsorbent material, such as activated carbon to adsorb contaminants such as heavier hydrocarbon contaminants without the removal of lighter hydrocarbons. Prasad requires that a means for removing moisture from the feed gas be provided because high moisture levels generally limit the ability of activated carbon adsorbents to retain their adsorptive capacity for heavy hydrocarbons.

Generally, thermal swing processes utilize the process steps of adsorption at a low temperature, regeneration at an elevated temperature with a hot purge gas and subsequent cooling down to the adsorption temperature. One process for drying gases generally exemplary of thermal swing processes is described in U.S. Pat. No. 4,484,933, issued to Cohen. The patent describes basic thermal swing processing steps coupled with the use of an auxiliary adsorber bed for improving the regeneration step. Thermal swing processes are often used for drying gases and liquids and for purification where trace impurities are to be removed. Often, thermal swing processes are employed when the components to be adsorbed are strongly adsorbed on the adsorbent, i.e., water, and thus, heat is required for regeneration.

It is an object of the invention, therefore, to provide an improved membrane system and process for overcoming the problem of degradation of permeability during gas production operations.

It is another object of the invention to provide a membrane system and process obviating the need for significant overdesign or for premature replacement of degraded membrane modules.

It is a further object of the invention to provide a membrane system and process for maintaining membrane permeability and minimizing the need for the interruption of gas producing operations for the treatment of membrane modules for restoration of the permeability characteristics thereof.

SUMMARY OF THE INVENTION

By the present invention, an adsorption process is provided for rejecting heavy hydrocarbons from a natural gas stream comprising carbon dioxide and heavy hydrocarbons prior to the introduction of the natural gas stream to a membrane unit for the separation of carbon dioxide from the natural gas. The process employs a selective adsorbent consisting of a high silica zeolite which, surprisingly, is able to retain its ability to adsorb heavy hydrocarbons in the presence of a wet gas comprising light hydrocarbons. Furthermore, the process produces a purified gas stream which is substantially free of heavy hydrocarbons and thus avoids the problem of initial membrane capacity losses disclosed in the prior art. Still further, the selective adsorbent is regenerable and applicant discloses a process wherein the selective adsorbent is regenerated with a portion of the non-permeate gas from the membrane unit.

In a broad aspect of the present invention there is provided an adsorption process for the rejection of heavy hydrocarbons from a light hydrocarbons gas stream comprising heavy hydrocarbons and carbon dioxide. The process comprises passing the light hydrocarbon gas stream to an adsorption zone. The adsorption zone contains a regenerable adsorbent comprising a high silica zeolite. The regenerable adsorbent is selective for the adsorption of the heavy hydrocarbons. The adsorption zone provides an effluent stream or a purified stream being essentially free of the heavy hydrocarbons. The purified stream is passed to a membrane zone to provide a permeate stream comprising carbon dioxide and a non-permeate stream having a reduced amount of carbon dioxide relative to the light hydrocarbon gas stream. At least a portion of the non-permeate stream is heated to provide a heated regeneration stream. The heated regeneration stream is used to regenerate the regenerable adsorbent and a spent regenerant stream comprising heavy hydrocarbons is recovered.

In another embodiment, the present invention is a process for rejecting heavy hydrocarbons from a natural gas stream comprising light hydrocarbons, heavy hydrocarbons, carbon dioxide, and water. The process comprises contacting the natural gas stream with a regenerable adsorbent comprising a zeolite molecular sieve having a silica to alumina ratio greater than 20 and a pore opening greater than about 4.5 Angstroms to provide a purified gas stream essentially free of heavy hydrocarbons and regenerating said regenerable adsorbent.

DETAILED DESCRIPTION OF THE INVENTION

Figure 1:
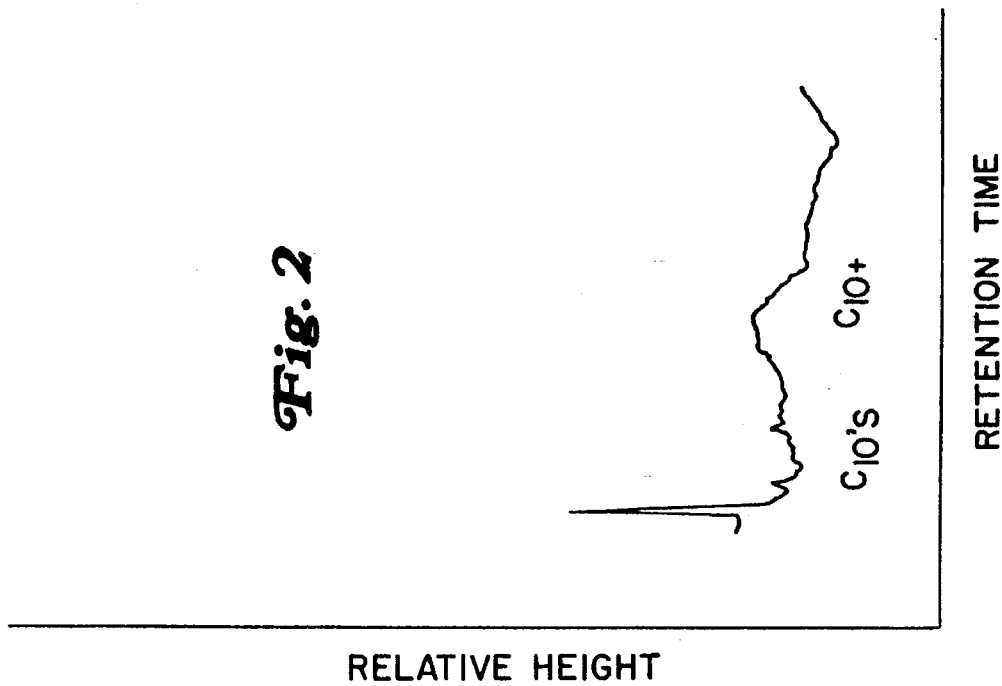
FIG. 1 is a gas chromatographic trace of a feed gas showing $C_{10}+$ components.

The invention is useful for the rejection of heavy hydrocarbons from a natural gas stream over a regenerable adsorbent to provide a purified natural gas stream which can be subsequently processed in a membrane unit for the further removal of other gases such as carbon dioxide. The purified natural gas stream produced by the process of this invention is essentially free of heavy hydrocarbons such as $C_{10}+$ hydrocarbons, where essentially free means a concentration of heavier hydrocarbons which is less than 100 ppm-vol, and preferably where the concentration of heavy hydrocarbons is less than about 10 ppm-vol. The purified natural gas stream may be passed to a membrane separation unit to provide a permeate gas stream comprising the associated gas and a non-permeate gas comprising light hydrocarbons. At least a portion of non-permeate gas can be employed to regenerate the regenerable adsorbent in a thermal swing adsorption sequence. Preferably, the natural gas stream comprises heavy hydrocarbons in an amount greater than about 500 ppm and more preferably the natural gas stream comprises about 500 ppm to about 1 wt-% heavy hydrocarbons. Preferably the natural gas stream comprises water in an amount greater than about 50 ppm-wt and less than saturation levels.

The thermal swing process of the present invention relates to conventional thermal swing processing in which each bed of an adsorption zone undergoes, on a cyclic basis, adsorption at an adsorption temperature wherein the more readily adsorbable component(s) in the feedstream are selectively adsorbed to provide an adsorption effluent stream enriched in the less readily adsorbable components, regeneration at a desorption temperature that is higher than the adsorption temperature which is conducted by passing a purge gas at an elevated temperature, i.e., equal to or higher than the desired desorption temperature through the bed, and cooling the bed to the adsorption temperature by passing a purge gas therethrough. Such process steps are disclosed, for example, in above-cited U.S. Pat. No. 4,484,933 hereby incorporated by reference.

It is to be understood that the adsorption zones of the present invention contain adsorption beds containing adsorbent suitable for adsorbing the particular components to be adsorbed therein. As the capacity of the adsorber bed for the more readily adsorbable component is reached, that is, preferably before a substantial portion of the leading adsorption front has passed through the first adsorption bed, the feedstream is directed to another bed in the adsorption zone. It is to be also understood that the term "countercurrent" denotes that the direction of gas flow through the adsorption bed, is countercurrent with respect to the direction of feedstream flow. Similarly, the term "cocurrent" denotes flow in the same direction as the feedstream flow. The purge gas is at least partially comprised of an effluent stream, e.g., the adsorption effluent stream from the adsorption bed, which comprises the less readily adsorbable component. The term "enriched" is intended to be with reference to the feedstream composition unless otherwise noted.

It will also be understood that the invention can be carried out using a suitable adsorbent material in the adsorption bed having a selectivity for various components of a feedstream over other such components, thereby providing a less readily adsorbable component and a more readily adsorbable component. In the present invention, the more readily adsorbable components are heavy hydrocarbons and water and the less readily adsorbable components are methane and carbon dioxide. Suitable adsorbents known in the art and commercially available include crystalline molecular sieves, activated carbons, activated clays, silica gels, activated aluminas and mixtures thereof. The crystalline molecular sieves include zeolitic molecular sieves.

Zeolitic molecular sieves in the calcined form may be represented by the general formula;

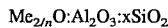

$$Me_{2/n}O:Al_2O_3:xSiO_2$$

where Me is a cation, x has a value from about 2 to infinity, and n is the cation valence. Typical well-known zeolites which may be used include: chabazite—also referred to as zeolite D, clinoptilolite, EMC-2, zeolite L, ZSM-5, ZSM-11, ZSM-18, ZSM-57, EU-1, offretite, faujasite, ferrierite, mordenite, zeolite A, ZK-5, zeolite rho, zeolite Beta, boggsite, and silicalite. The adsorbent of the present invention will be selected from these zeolite adsorbents and mixtures thereof. It is desirable to reduce the aluminum content in the zeolite structure, thereby reducing the affinity of water to the zeolite while retaining its ability to retain its hydrocarbon adsorption capacity in the presence of fairly high moisture levels. For these reasons, zeolites suitable for use according to the present invention are those having a high silica content, i.e., those having silica to alumina ratios preferably greater than 20. Preferably, adsorbents which are naturally occurring or are synthetically produced with a silica to alumina ratio less than about 20 will be modified by conventional means such as steaming, acid extraction, fluoride treatment and the like to increase the silica to alumina ratio to greater than about 20. Faujasites having a silica to alumina ratio greater than 20 are preferred for use with the present invention. One such high silica zeolite is silicalite, as the term used herein includes both the silicapolymorph disclosed in U.S. Pat. No. 4,061,724 and also the F-silicalite disclosed in U.S. Pat. No. 4,073,865, which are hereby incorporated by reference. Detailed descriptions of some of the above identified zeolites may be found in D. W. Breck, *ZEOLITE MOLECULAR SIEVES*, John Wiley and Sons, New York, 1974, hereby incorporated by reference.

The term pore opening refers to the pore diameter of the adsorbent within the crystal structure of the adsorbent. Zeolite molecular sieves have pores of uniform opening, ranging from about 3 Angstroms to about 10 Angstroms, which are uniquely determined by the unit structure of the crystal. These pores will completely exclude molecules which are larger than the opening of the pore. For example, linear paraffins are separated from branched-chain and cyclic hydrocarbons by adsorption on a so-called 5A molecular sieve. The pore opening is such that among the hydrocarbons only linear molecules can pass, while branched-chain molecules are excluded. In the process of the present invention, it is preferred that the pore opening of the high-silica zeolites be greater than about 4.3 Angstroms, and more preferably that the pore opening of the high-silica zoolites be greater than about 4.5 Angstroms. The pore opening of naturally occurring zeolites and synthetically produced zeolitic molecular sieves may be increased by any conventional means such as cation exchange, acid leaching and the like.

The preferred adsorbents for use with the present invention include synthetic and naturally occurring zeolites with a silica to alumina ratio greater than 20 and having a pore opening larger than 4.3 Angstroms. More particularly, synthetic and naturally occurring zeolites having a FAU structure and/or MFI structure as defined in the "Atlas of Zeolite Structure Types," by W. M. Meier and D. H. Olson, issued by the Structure Commission of the International Zeolite Association, (1987), on pages 53–54 and pages 91–92, are preferred. The above reference is hereby incorporated by reference. Most preferably, the high silica zeolite adsorbent for use with the present invention will have a silica to alumina ratio greater than about 20 and a pore opening greater than about 4.5 Angstroms.

It is often desirable when using crystalline molecular sieves that the molecular sieve be agglomerated with a binder in order to ensure that the adsorbent will have suitable particle size. Although there are a variety of synthetic and naturally occurring binder materials available such as metal oxides, clays, silicas, aluminas, silica-aluminas, silica-zirconias, silica-thorias, silica-berylias, silica-titanias, silica-alumina-thorias, silica-alumina-zirconias, mixtures of these and the like, silica binders are preferred. Silica is preferred because it may be employed to agglomerate the molecular sieve without substantially altering the adsorptive properties of the zeolite. The choice of a suitable binder and methods employed to agglomerate the molecular sieves are generally known to those skilled in the art and need not be further described herein.

The adsorption process operates most efficiently when the adsorption temperature, the temperature at which the adsorption step takes place, is preferably in the range of about 5° C. to about 80° C. The desorption temperature, the temperature at which the desorption effluent is recovered, is preferably in the range of about 120° C. to about 315° C.

The following examples are provided to illustrate the present invention and is not intended to limit the scope of the claims that follows.

EXAMPLES

GENERAL

An adsorption pilot plant having 2 vertical chambers approximately 1.52M in length and having an internal diameter of 26.6 mm were loaded with 477 grams of a high silica zeolite adsorbent, in the form of 1/16 inch etrudates. Each chamber operated as a separate adsorption bed such that while one chamber was in an adsorption mode, the other chamber was regenerated. The chambers were cycled manually between adsorption and regeneration. The feed gas was a slip stream from an operating natural gas well at a pressure ranging between 3.9 and 4.2 MPa and a temperature ranging between about 29° C. and 34° C. The rate of the feed gas averaged between about 7 Nm³/H (260 SCFH) and 7.2 Nm³/H (267 SCFH). During regeneration, a portion of the adsorption effluent or purified gas was heated to a temperature of about 176° C. and passed to one end of the chamber undergoing regeneration. The spent regenerant gas, recovered from the opposite end of the chamber undergoing regeneration, was cooled and passed through a knockout drum to remove any condensed liquids such as water and hydrocarbons from the spent regenerant gas. The cooler consisted of a water-jacketed coil of 4.6 mm ID stainless steel tubing which returned the spent regenerant gas to ambient temperature. On-site gas chromatographs which were adapted with photoionization detectors (PID) and with flame ionization detectors (FID) were employed to analyze the feed gas and the purified gas. Although it was expected that the compositions would be extremely difficult to quantify, the objective was to determine that the feed gas was purified by the adsorption unit. The feed natural gas composition is shown in Table 1.

TABLE 1

AVERAGE COMPOSITION OF FEED NATURAL GAS

| COMPONENT | VOL-% |
|---|---|
| Carbon dioxide | 50.0 |
| Nitrogen | 8.0 |
| Methane | 34.0 |
| Ethane | 3.7 |
| Propane | 1.6 |
| Butanes | 1.0 |
| Heavy Hydrocarbons | 0.1 |

Example I

FIG. 1 shows the gas chromatograph (GC) response curve from the GC with FID for the feed gas at the above conditions. In the non-aromatic portion of the tracers there are clearly peaks representative of $C_{10}+$ components.

Figure 2:
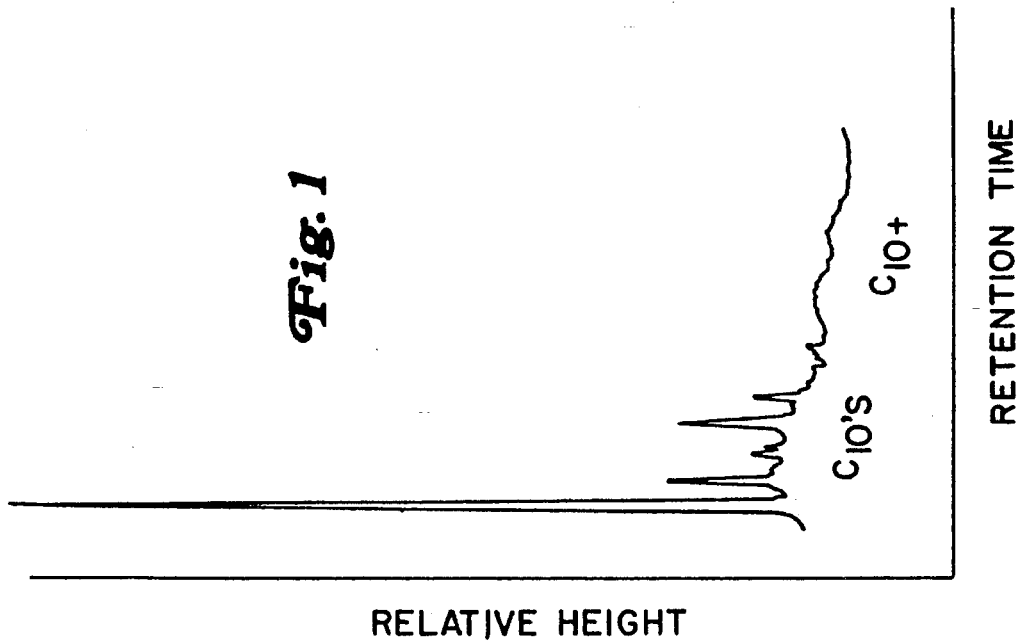
FIG. 2 is a gas chromatographic trace of a purified gas showing $C_{10}+$ components.

FIG. 2 shows the GC with FID trace for the purified gas stream. The absence of $C_{10}+$ peaks analyzed at the same sensitivity as that shown in FIG. 1 clearly showed that the feed gas has been depleted of the composition in the $C_{10}+$ range.

Example II

Figure 4:
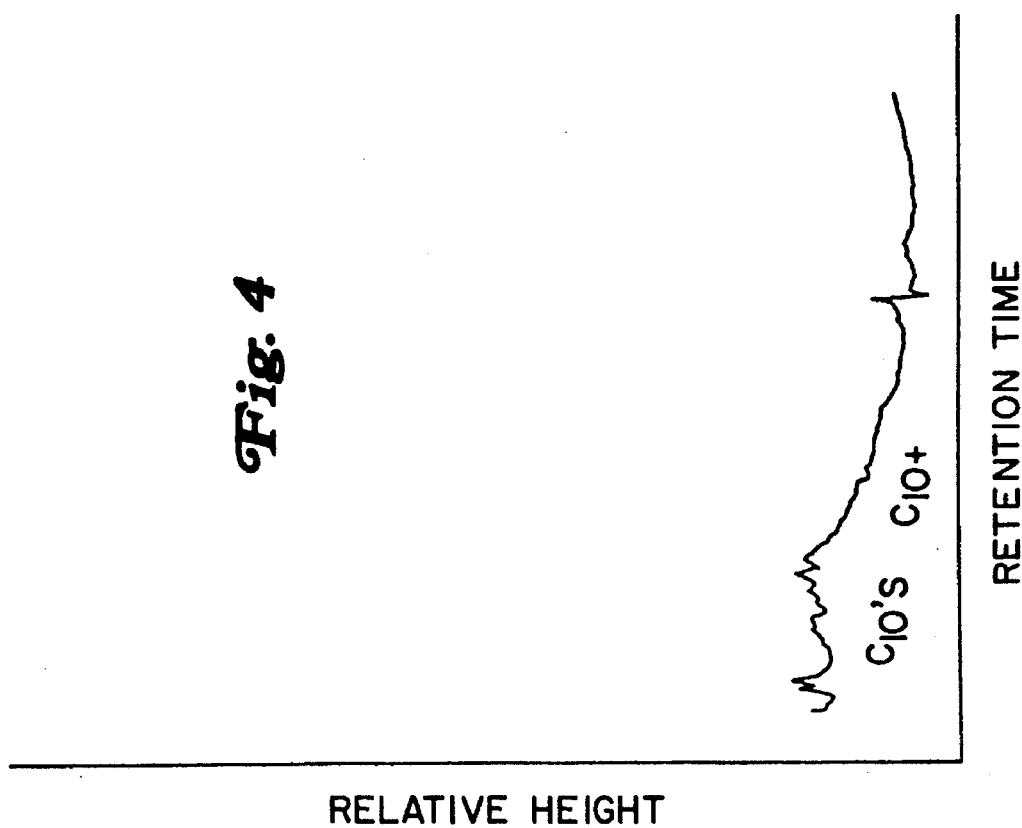
FIG. 4 is a gas chromatographic trace of a purified gas showing $C_{10}+$ aromatics.
Figure 3:
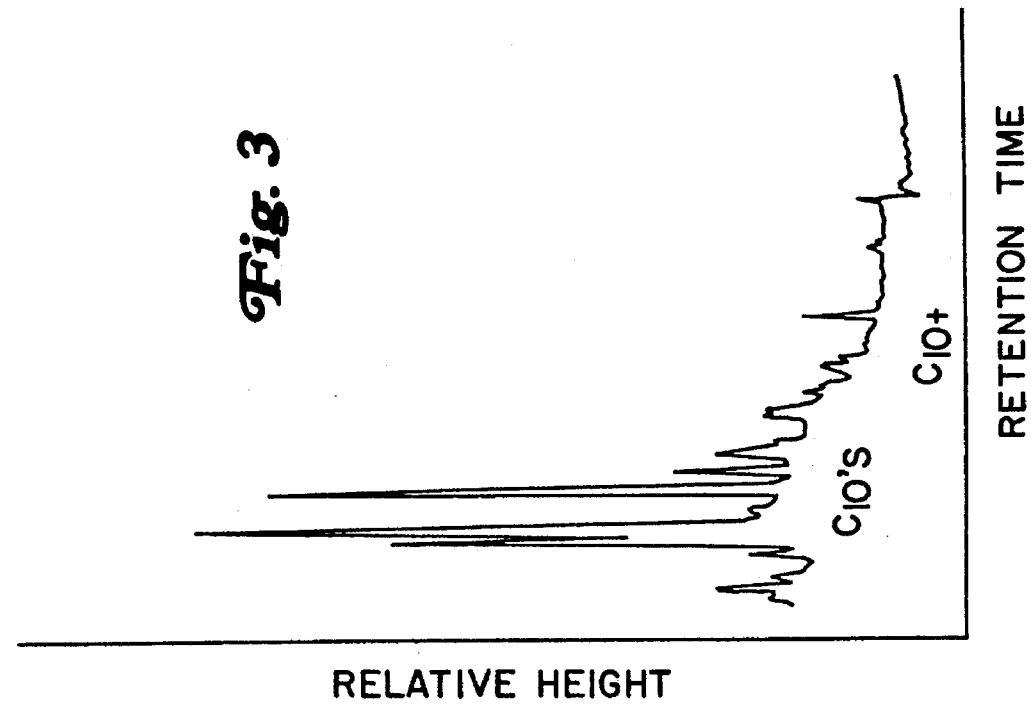
FIG. 3 is a gas chromatographic trace of a feed gas showing $C_{10}+$ aromatics.

FIG. 3 shows a gas chromatograph trace for the GC with the PID detector for the analysis of $C_{10}+$ aromatic components in the feed gas. FIG. 4 shows similar analysis for the $C_{10}+$ aromatic components in the purified gas stream from the 11th cycle of adsorption and regeneration. Again, the comparison of FIG. 3 and FIG. 4 in the $C_{10}+$ aromatic components has been essentially eliminated. Furthermore, the purified gas of the 11th cycle shows that the adsorbent performance was not degraded by the successive regenerations.

Example III

A sample of the liquid hydrocarbons collected in the knockout drum were analyzed on a GC with an FID detector at a high sensitivity. The liquid was found to comprise predominantly $C_5+$ hydrocarbons. About 10 wt-% of the liquid comprised $C_{10}$ and heavier hydrocarbons, including very heavy hydrocarbons having carbon numbers greater than 14.

Example IV

At the conclusion of the tests the adsorbent was removed from the chambers and analyzed. The adsorbent samples did not indicate any degradation of the structure often associated with zeolites in natural gas service.

We claim:

1. A process for rejecting heavy hydrocarbons from a light hydrocarbon gas stream comprising methane and ethane, said heavy hydrocarbons including $C_{10+}$ hydrocarbons, water, and carbon dioxide, said process comprising:

a) passing the light hydrocarbon gas stream to an adsorption bed containing a regenerable adsorbent comprising a high silica zeolite having a silica to alumina ratio greater than about 20 and selective for the adsorption of said heavy hydrocarbons, to provide an adsorption effluent stream essentially free of said heavy hydrocarbons;

b) passing said adsorption effluent to a membrane zone to provide a non-permeate stream having a reduced amount of carbon dioxide relative to the light hydrocarbon gas stream; and c) regenerating said adsorbent.

2. The process of claim 1 wherein said regenerable adsorbent is selected from the group consisting of silicalite, zeolite Beta, boggsite, chabasite, faujasite, EMC-2, zeolite L, mordenite, offretite, ferrierite, ZSM-5, ZSM-11, ZSM-18, ZSM-57, EU-1, zeolite A, ZK-5, zeolite Rho, and mixtures thereof.

3. The process of claim 2 wherein said regenerable adsorbent comprises a zeolite molecular sieve having a silica to alumina ratio greater than about 20 and a pore opening greater than about 4.5 Angstroms.

4. The process of claim 3 wherein said regenerable adsorbent comprises a zeolite molecular sieve having a FAU structure.

5. The process of claim 3 wherein said regenerable adsorbent comprises a zeolite molecular sieve having a MFI structure.

6. The process of claim 3 wherein said regenerable adsorbent comprises silicalite.

7. The process of claim 1 further comprising:

a) contacting said adsorbent with at least a portion of said non-permeate stream to regenerate said adsorbent and recovering a spent regeneration gas stream;

b) cooling said regeneration gas stream to provide a cooled spent regeneration gas stream; and, c) combining said cooled spent regeneration gas stream with said non-permeate stream.

8. A process for rejecting heavy hydrocarbons from a natural gas stream comprising light hydrocarbons including methane, ethane, propane, and butane, heavy hydrocarbons including $C_{10+}$ hydrocarbons, carbon dioxide, and water, said process comprising:

a) contacting the natural gas stream with a regenerable adsorbent comprising a high silica zeolite molecular sieve selective for the adsorption of said heavy hydrocarbons, said molecular sieve having a silica to alumina ratio greater than 20 and a pore opening greater than about 4.5 Angstroms to provide a purified gas stream essentially free of heavy hydrocarbons; and, b) regenerating said regenerable adsorbent.

9. The process of claim 8 further comprising passing said purified gas stream to a membrane zone to provide a non-permeate stream, heating at least a portion of the non-permeate stream to provide a heated regeneration gas stream, and contacting the regenerable adsorbent with the heated regeneration gas stream.

10. The process of claim 8 wherein the natural gas stream comprises heavy hydrocarbons in an amount ranging from about 500 ppm-wt to about 1 wt-%.

11. The process of claim 8 wherein the natural gas stream comprises water in an amount ranging from about 50 ppm-wt to about saturation.

12. The process of claim 8 wherein said regenerating of said regenerable adsorbent is carried out at a temperature ranging from about 120° C. to about 315° C.

13. A cyclic process for rejecting heavy hydrocarbons from a natural gas stream including methane, ethane, propane and butane, heavy hydrocarbons including $C_{10+}$ hydrocarbons, carbon dioxide, and water, prior to introducing said natural gas stream to a membrane unit for the separation of carbon dioxide from the natural gas stream, said process comprising:

a) contacting the natural gas stream comprising from about 500 ppm to about 1 wt-% heavy hydrocarbons with a regenerable adsorbent comprising a high silica zeolite molecular sieve having a silica to alumina ratio greater than 20 and a pore opening greater than about 4.5 Angstroms, said regenerable adsorbent being selected from at least one of the group consisting of silicalite, zeolite Beta, boggsite, chabasite, faujasite, EMC-2, zeolite L, mordenite, offretite, ferrierite, ZSM-5, ZSM-11, ZSM-18, ZSM-57, EU-1, zeolite A, ZK-5, zeolite Rho, and mixtures thereof to provide a purified gas stream essentially free of said heavy hydrocarbons;

b) terminating the contacting of the natural gas stream with the regenerable adsorbent and contacting said regenerable adsorbent with at least a portion of a non-permeate stream from the membrane zone to regenerate said adsorbent and recovering a spent regeneration gas stream;

c) cooling said regeneration gas stream to provide a cooled spent regeneration gas stream; and, d) combining said cooled spent regeneration gas stream with said non-permeate stream.

14. The process of claim 13 wherein said purified gas comprises less than about 100 ppm-vol of heavy hydrocarbons.

* * * * *